US012611633B2

(12) United States Patent
Matsui et al.

(10) Patent No.: US 12,611,633 B2
(45) Date of Patent: Apr. 28, 2026

(54) FILTER EVALUATING DEVICE, PURIFYING DEVICE, AND FILTER EVALUATING METHOD

(71) Applicant: Yokogawa Electric Corporation, Tokyo (JP)

(72) Inventors: Yasuhiro Matsui, Musashino (JP); Hiroyuki Katayama, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 275 days.

(21) Appl. No.: 18/283,991

(22) PCT Filed: Feb. 15, 2022

(86) PCT No.: PCT/JP2022/005995
§ 371 (c)(1),
(2) Date: Sep. 25, 2023

(87) PCT Pub. No.: WO2022/201978
PCT Pub. Date: Sep. 29, 2022

(65) Prior Publication Data
US 2024/0165565 A1 May 23, 2024

(30) Foreign Application Priority Data

Mar. 26, 2021 (JP) ................................. 2021-054161

(51) Int. Cl.
| | |
|---|---|
| *G01N 15/08* | (2006.01) |
| *B01D 35/143* | (2006.01) |
| *B01D 65/10* | (2006.01) |
| *G01N 15/02* | (2006.01) |
| *G01N 33/18* | (2006.01) |

(52) U.S. Cl.
CPC ......... *B01D 65/10* (2013.01); *B01D 35/1435* (2013.01); *G01N 15/0272* (2013.01); *G01N 33/18* (2013.01)

(58) Field of Classification Search
CPC ................................................ G01N 2015/084
See application file for complete search history.

(56) References Cited

U.S. PATENT DOCUMENTS

| | | | | |
|---|---|---|---|---|
| 5,594,161 | A * | 1/1997 | Randhahn ............ | B01D 29/114 |
| | | | | 73/38 |
| 2004/0110205 | A1* | 6/2004 | Wang ....................... | B82Y 5/00 |
| | | | | 435/6.12 |
| 2010/0097605 | A1* | 4/2010 | Murakami ........... | B01D 65/102 |
| | | | | 356/337 |

FOREIGN PATENT DOCUMENTS

| | | | | |
|---|---|---|---|---|
| JP | 2014-8435 A | 1/2014 | | |
| WO | WO-2007046095 A2 * | 4/2007 | ........... | B01D 65/102 |
| WO | 2008/047926 A1 | 4/2008 | | |

OTHER PUBLICATIONS

Japanese Office Action dated Apr. 9, 2024 for Japanese Patent Application No. 2021-054161; English machine translation.
Australian Office Action dated Sep. 9, 2025 for Australian Patent Application No. 2022243654.

* cited by examiner

*Primary Examiner* — Alexander A Mercado
(74) *Attorney, Agent, or Firm* — RANKIN, HILL & CLARK LLP

(57) ABSTRACT

A filter evaluating device including a controller configured to evaluate the integrity of a filter based on a measurement result of measuring microorganisms in treated water filtered by the filter, and output information regarding an evaluation result.

9 Claims, 5 Drawing Sheets

*FIG. 4*

FILTER EVALUATING DEVICE, PURIFYING DEVICE, AND FILTER EVALUATING METHOD

CROSS-REFERENCE TO RELATED APPLICATION

The present application claims priority to and the benefit of Japanese Patent Application No. 2021-54161 filed Mar. 26, 2021, the entire contents of which are incorporated herein by reference.

TECHNICAL FIELD

The present disclosure relates to a filter evaluating device, a purifying device, and a filter evaluating method.

BACKGROUND

Conventional methods of determining whether or not there is a problem with a filter in a purifying device by using a pressure decay test (PDT) are known (see, for example, Patent Literature (PTL) 1).

CITATION LIST

Patent Literature

PTL 1: JP 2014-8435 A

SUMMARY

A filter evaluating device according to at least one embodiment comprises a controller configured to evaluate the integrity of a filter based on a measurement result of measuring microorganisms in treated water filtered by the filter, and output information regarding an evaluation result.

A purifying device according to at least one embodiment comprises: the filter evaluating device; the filter; and a measurer configured to measure microorganisms in water filtered by the filter and output the measurement result to the filter evaluating device.

A filter evaluating method according to at least one embodiment comprises: evaluating the integrity of a filter based on a measurement result of measuring microorganisms in treated water filtered by the filter; and outputting information regarding an evaluation result.

BRIEF DESCRIPTION OF THE DRAWINGS

In the accompanying drawings:

FIG. 4 is a schematic diagram illustrating an example configuration for collective sampling from a plurality of filters connected in parallel.

DETAILED DESCRIPTION

Figure 1:
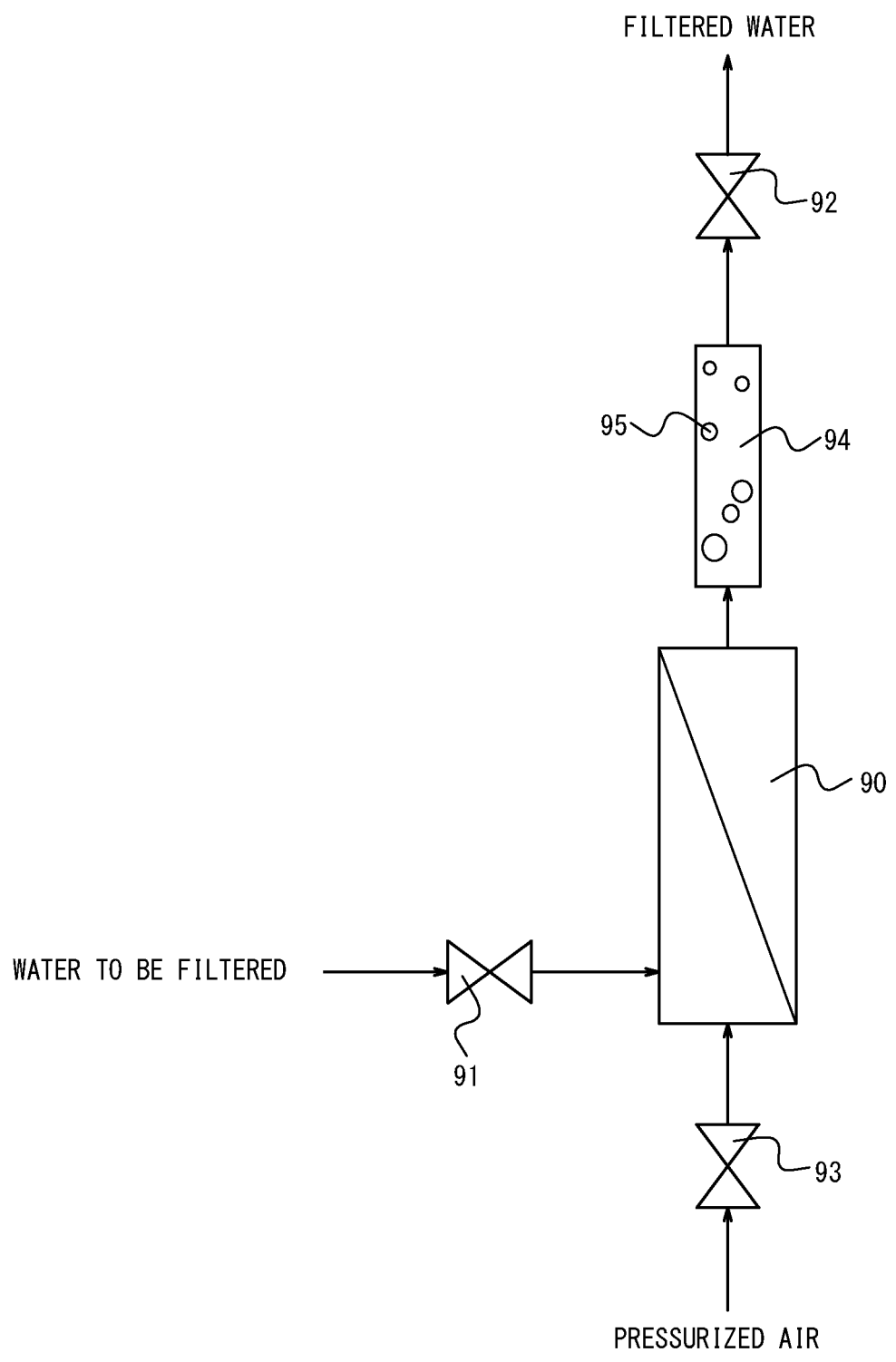
FIG. 1 is a conceptual diagram of implementation of PDT according to a comparative example.

Purifying devices need to be stopped to perform PDT. Stopping a purifying device reduces the convenience of the purifying device by reducing the availability of the purifying device, for example. There is a demand for improvement of convenience of purifying devices. It would be helpful to provide a filter evaluating device, a purifying device, and a filter evaluating method able to improve the convenience of purifying devices. According to the filter evaluating device, the purifying device, and the filter evaluating method of the present disclosure, the convenience of the purifying device having the filter is improved.

A filter evaluating device according to at least one embodiment comprises a controller configured to evaluate the integrity of a filter based on a measurement result of measuring microorganisms in treated water filtered by the filter, and output information regarding an evaluation result. In this way, the integrity of the filter may be evaluated while the purifying device is still in operation. As a result, the convenience of the purifying device that has the filter is improved.

According to an embodiment, the controller is configured to output an alarm regarding the filter when the treated water includes microorganisms having a particle size of a defined value or more, the defined value determined based on filtration performance of the filter. In this way, the need for maintenance such as filter replacement becomes clear. As a result, the convenience of the purifying device that has the filter is improved. According to an embodiment, the controller is configured to output an alarm regarding the filter when a specific variety of microorganism is detected as a microorganism in the treated water. In this way, the need for maintenance such as filter replacement becomes clear. As a result, the convenience of the purifying device that has the filter is improved.

A purifying device according to at least one embodiment comprises: the filter evaluating device; the filter; and a measurer configured to measure microorganisms in water filtered by the filter and output the measurement result to the filter evaluating device. In this way, the integrity of the filter may be evaluated while the purifying device is still in operation. As a result, the convenience of the purifying device that has the filter is improved.

According to an embodiment, the purifying device comprises the filter in a plurality, each connected in parallel with each other, and further comprises: a valve configured to allow the measurer to collectively sample treated water filtered by the plurality of filters from a pipe that merges flow on a secondary side of the plurality of filters. In this way, time, cost, and the like spent on evaluating the integrity of the filter may be reduced. As a result, the convenience of the purifying device that has the filter is improved.

A filter evaluating method according to at least one embodiment comprises: evaluating the integrity of a filter based on a measurement result of measuring microorganisms in treated water filtered by the filter; and outputting information regarding an evaluation result. In this way, the integrity of the filter may be evaluated while the purifying device is still in operation. As a result, the convenience of the purifying device that has the filter is improved.

Embodiments of the present disclosure are described below with reference to the drawings.

Comparative Example

As a comparative example, a method of evaluating the integrity of a filter using a pressure decay test (PDT) is described.

A membrane filtration system according to the comparative example has 36 series of filter units. In each series of filter units, water quality of membrane filtered water is monitored for poor quality due to rupture of a filter membrane, separation of seal material, or a problem in a machine or material that constitutes the filter unit, based on an inspection result according to PDT.

Operation of the membrane filtration system according to the comparative example is continuously controlled according to an operation sequence that includes filtration, backwash and chemically enhanced backwash (CEB) for each filter unit. Backwash means washing the filter unit using filtered water. CEB means washing the filter unit using a chemical.

A conceptual diagram of the implementation of PDT is illustrated as FIG. 1. A filter 90 to be inspected by PDT is configured to accept water to be filtered from a feed side (primary side) and output filtered water to a permeation side (secondary side). When the filter 90 filters water, a valve 91 on the primary side and a valve 92 on the secondary side are opened.

During the performing of PDT, the valve 92 on the primary side is closed. A valve 93, to which a pressurized air pipe is connected, is then opened. Accordingly, pressurized air is injected to pressurize the primary side of the filter 90. With the primary side of the filter 90 pressurized with air, pressure changes are monitored over a defined time period. When a rupture or damage is present in the filter membrane of the filter 90 or in mechanical components of a module including the filter 90, the pressurized air injected into the primary side leaks to the secondary side. When the pressurized air leaks, a decrease in pressure on the primary side or an increase in pressure on the secondary side is detected. By detecting changes in pressure on the primary side or the secondary side, a problem with the filter 90 may be detected. Further, air leaking to the secondary side becomes bubbles in water on the secondary side. When the piping on the secondary side includes a transparent pipe 94, air leaks may be visually observed as bubbles 95. Pressurized air may be injected to pressurize the secondary side of the filter 90. In such a case, a problem with the filter 90 may be detected by observing leakage on the primary side of the filter 90.

In order to pressurize the primary side of the filter and monitor pressure changes, operation of the membrane filtration system needs to be stopped. Stopping the membrane filtration system reduces the availability of the membrane filtration system and stopping and restarting operations and the like complicate control. There is a demand for evaluation of filter integrity, including detection of filter problems, to be performed while the membrane filtration system is in operation.

Further, according to Environmental Protection Agency (EPA), Membrane Filtration Guidance Manual, EPA 815-R-06-009, 2005, a membrane rupture diameter that is theoretically testable by PDT is 3 μm. A microorganism in water that corresponds to 3 μm diameter is *Cryptosporidium*. Accordingly, microorganisms that are filterable by the filter that is determined to be normal by the PDT test are *Cryptosporidium* size or microorganisms larger than *Cryptosporidium*. Conversely, a filter that is determined to be normal by testing with PDT is not able to filter microorganisms that have a diameter of less than 3 μm, for example bacteria such as *Escherichia coli* or viruses. In other words, inspection of filters by PDT cannot ensure a removal performance capable of removing microorganisms that have diameters less than 3 μm.

The theory of inspection by PDT is explained based on Equation 4.1 below. Equation 4.1 below specifies the relationship between the pressure $P_{test}$ of bubbles generated on the primary side of the filter by PDT, the shape correction factor κ of the pores in the filter, the surface tension σ generated at the air-liquid interface, the liquid-membrane contact angle θ, the maximum backpressure $BP_{max}$ generated on the secondary side of the filter, and a unit conversion factor for a membrane rupture diameter of 3 μm. The unit conversion factor is expressed as a numerical value 0.193 in Equation 4.1.

[Num. 1]

$$P_{test}=(0.193 \cdot \kappa \cdot \sigma \cdot \cos\ \theta)+BP_{max} \qquad \text{Equation 4.1}$$

Figure 2:
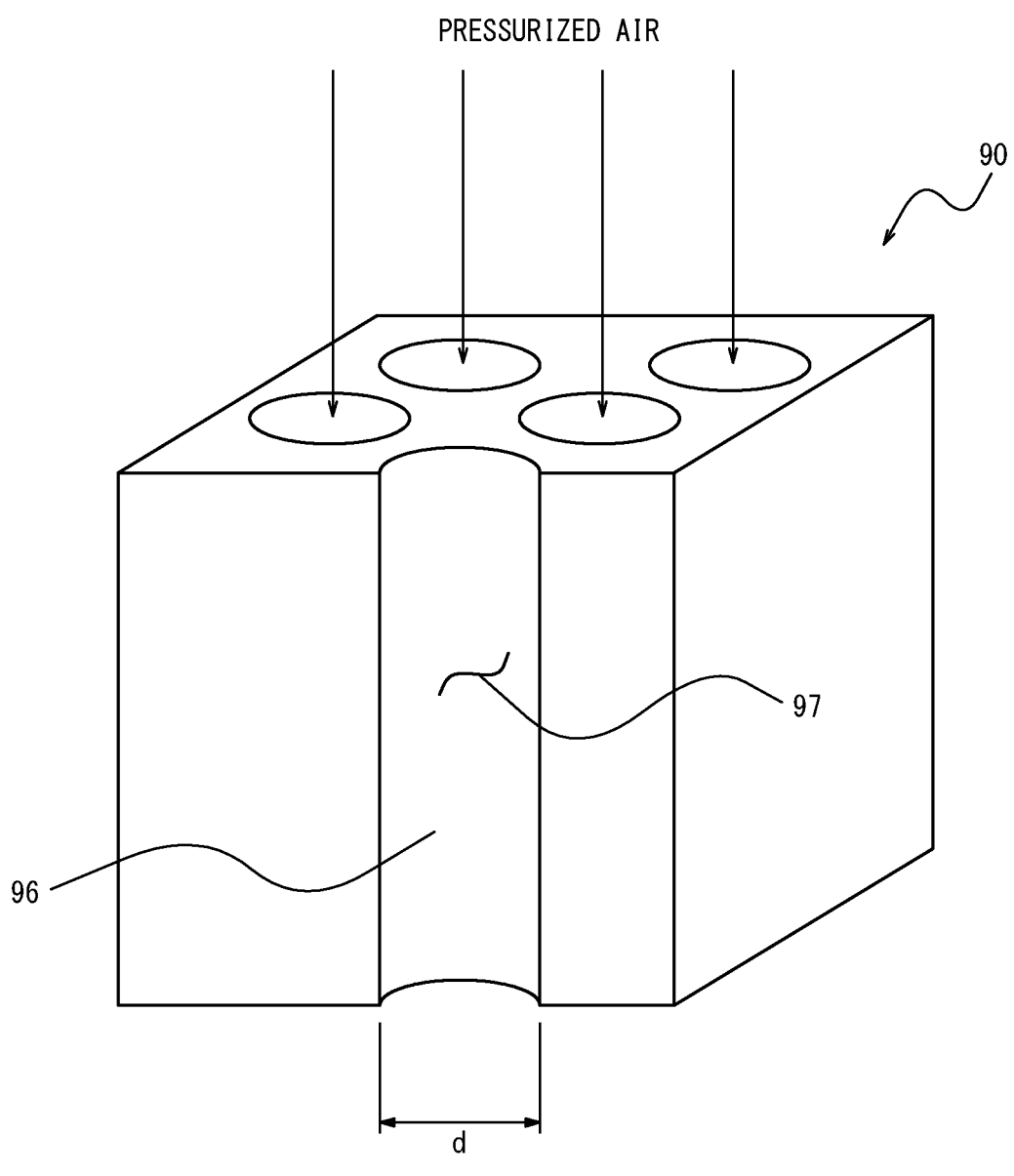
FIG. 2 is a cross-sectional schematic diagram of a membrane structure of a filter subject to PDT.

Where: $P_{test}$=minimum test pressure (psi)
  κ=pore shape correction factor (dimensionless)
  σ=surface tension at the air-liquid interface (dynes/cm)
  θ=liquid-membrane contact angle (degrees)
  $BP_{max}$=maximum backpressure on the system during the test (psi)
  0.193=constant that includes the defect diameter (i.e., 3 μm resolution requirement) and unit conversion factors Equation 4.1 is an application of bubble point theory, and is derived from Equation B.1 below. Bubble point theory is a pressure theory according to which bubbles may be held due to the viscosity and surface tension of water. In bubble point theory, a pressure $P_{bp}$ able to hold a bubble is proportional to the surface tension 6 and inversely proportional to the capillary diameter $d_{cap}$. FIG. 2 illustrates a cross-sectional schematic diagram of the structure of the membrane of the filter 90 subject to PDT. The membrane of filter 90 has pores 96. The diameter of the pores 96 is indicated by d in FIG. 2. Details of the membrane of the filter are described in Appendix B of the document EPA 815-R-06-009, mentioned above. When a rupture 97 has occurred in the membrane, the pressure that may be held by the holes 96 in the membrane and the rupture 97 that has occurred in the membrane is expressed by Equation B.1 below. Equation B.1 is converted to Equation 4.1 by converting each parameter in Equation B.1 to units and applying the coefficient corresponding to a 3 μm diameter bubble.

[Num. 2]

$$P_{bp} = \frac{4 \cdot \sigma \cdot \cos\theta}{d_{cap}} \qquad \text{Equation B.1}$$

Where: $P_{bp}$=bubble point pressure
  σ=surface tension at the air-liquid interface
  θ=liquid-membrane contact angle
  $d_{cap}$=capillary diameter During each of the above-mentioned operational sequences of filtration, backwash, and CEB, a sequence of PDT runs is incorporated to evaluate filter integrity. When PDT is performed, each sequence of operation of the membrane filtration system is stopped. In other words, the performing of PDT reduces the availability of the membrane filtration system. Further, control of the operation sequence becomes complex to incorporate the PDT sequence. Further, additional dedicated equipment is needed to perform PDT.

As discussed above, in the membrane filtration system according to the comparative example, performing PDT to evaluate filter integrity has effects on the system such as reduced availability, increased control complexity, additional equipment requirement, and the like. In contrast, according to a filter evaluating device 30 and a filter evaluating method according to an embodiment of the present disclosure, as described below, the integrity of a filter 10 is evaluated while a purifying device 1 including the filter 10 (see FIG. 3) remains in operation. In this way, performing the evaluation of the integrity of the filter 10 is less likely to affect the availability and the control of the operation sequence. Further, dedicated equipment is not required to evaluate the integrity of the filter 10. As a result, the convenience of the purifying device 1 is improved.

Further, even when the integrity of the physical function of membrane filtration is ascertained by conducting PDT in the membrane filtration system according to the comparative example, only the absence of *Cryptosporidium* and other microorganisms having a particle size of 3 μm or more in the filtered water, or a removal rate of 99.99% (4 log reduction) for *Cryptosporidium*, is confirmed. That is, PDT is only a method of ascertaining the mechanical and physical properties of filtration membranes and makes only a very limited contribution to the control of pathogenic microorganisms in water. In contrast, the filter evaluating device 30 and the filter evaluating method according to an embodiment of the present disclosure, as described below, relate to the acute toxicity of filtered water in a membrane filtration system, and sampling is performed on filtered water focusing on genes derived from microorganisms such as viruses, bacteria, protozoa, and the like that may be pathogenic to the human body. Sampling checks for the presence or absence of pathogenic microorganisms and quantitatively measures pathogenic microorganisms. The measurement of pathogenic microorganisms ascertains the performance of the membrane filtration system in stopping pathogenic microorganisms. Further, by ascertaining the current performance of the membrane filtration system and the quality of the filtered water, comparison to the performance that the membrane filtration system is intended to exhibit is possible. The membrane filtration system is controllable based on the current performance.

The purifying device 1, the filter evaluating device 30, and the filter evaluating method according to an embodiment of the present disclosure are described below.

(Example Configuration of Purifying Device 1)

The purifying device 1 according to an embodiment of the present disclosure may be employed in water treatment infrastructure such as water purification plants, sewage treatment plants, water reclamation facilities, seawater desalination facilities, and the like. Ensuring the quality of water treated by membranes applied in water treatment infrastructure is necessary for membranes such as microfiltration (MF) membranes, ultrafiltration (UF) membranes, nanofiltration (NF) membranes, reverse osmosis (RO) membranes, and the like. To ensure water quality, ascertaining membrane treatment function is necessary, in terms of inhibition of *Cryptosporidium* and other protozoa, which are highly toxic among microorganisms in water.

Figure 3:
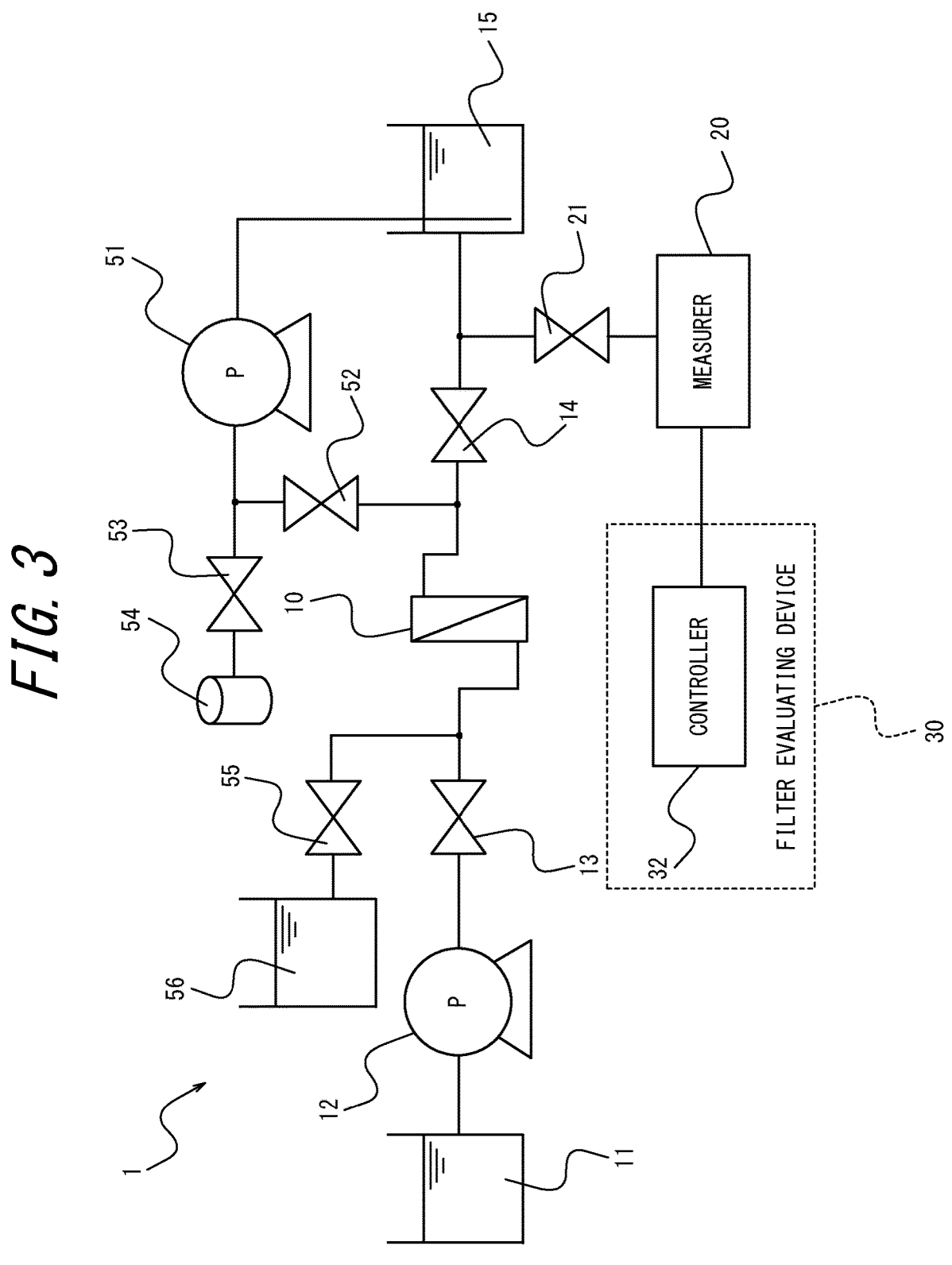
FIG. 3 is a schematic diagram of an example configuration of a purifying device according to an embodiment.

As illustrated in FIG. 3, the purifying device 1 according to an embodiment of the present disclosure includes the filter 10, a measurer 20 that measures microorganisms in water filtered by the filter 10, and a controller 32.

<Filter 10>

The filter 10 includes a membrane that filters water. The membrane of the filter 10 may include organic membrane material, inorganic membrane material, and the like. Organic membrane material may include, for example, polyvinylidene difluoride (PVDF), polyethylene (PE), polytetrafluoroethylene (PTFE), polypropylene (PP), cellulose acetate (CA), polyacrylonitrile (PAN), polyimide (PI), polysulfone (PS), polyethersulfone (PES), and the like. Inorganic membrane material may include, for example, ceramic membranes using aluminum oxide (alumina: $Al_2O_3$), zirconium dioxide (zirconia: $ZrO_2$), titanium dioxide (titania: $TiO_2$), and the like. Inorganic membrane material may include stainless steel (steel use stainless (SUS)) or glass (shirasu porous glass (SPG)) membranes.

The membrane is configured as a module to filter water at the filter 10. The module may be configured to include hollow fibers made using organic membrane material. The module may be configured in a flat membrane spiral shape. The module may be configured to be applicable to pressurized systems where water is filtered under pressure. The module may be configured to be applicable to an immersion filtration system in which the module is immersed in water in a tank. The module may be configured to be a monolithic shape, a flat membrane shape, or the like, made using inorganic membrane material.

<Controller 32>

The controller 32 controls each component. Further, the controller 32 obtains information from each component of the purifying device 1 and outputs information to each component. The controller 32 evaluates the integrity of the filter 10, as described below. The controller 32 may be considered part of the filter evaluating device 30. The filter evaluating device 30 may be included in the purifying device 1 or may be configured to be separate from the purifying device 1. The controller 32 may be configured to include a processor, such as a central processing unit (CPU). The controller 32 may realize a defined function by having a processor execute a defined program. The controller 32 may include a memory. The memory may store information used in the operation of the controller 32, programs to realize functions of the controller 32, and the like. The memory may function as the working memory of the controller 32. The memory may be configured as a semiconductor memory, for example. The memory may be included in the controller 32 or may be configured to be separate from the controller 32.

The purifying device 1 operates in filtration mode. In the filtration mode, the purifying device 1 filters untreated water stored in a water storage tank 11 or the like at the filter 10 and feeds filtered treated water to a water storage tank 15 or the like. The purifying device 1 further includes a filtration pump 12 that feeds untreated water stored in the water storage tank 11 or the like to the primary side of the filter 10, a valve 13 connected between the primary side of the filter 10 and the filtration pump 12, and a valve 14 connected to the secondary side of the filter 10. Untreated water is fed into the primary side of the filter 10 by the filtration pump 12 while the valve 13 is open, and is filtered by the filter 10 to become treated water. The treated water is fed from the secondary side of the filter 10 to the water storage tank 15 or the like while the valve 14 is open. In other words, in the filtration mode, the controller 32 of the purifying device 1 causes the valve 13 and the valve 14 to be open and the filtration pump 12 to be driven.

The purifying device 1 may operate in a backwash mode. In the backwash mode, the purifying device 1 backwashes the filter 10 by feeding washing water to the secondary side of the filter 10 and allowing the washing water to flow from the secondary side to the primary side. For example, treated water stored in the water storage tank 15 or the like may be used as washing water. Further, water that backwashes the filter 10 is fed to a waste tank 56 as waste liquid. The purifying device 1 further includes a backwash pump 51 that feeds washing water such as treated water stored in the water storage tank 15 to the secondary side of the filter 10, and a valve 52 connected between the secondary side of the filter 10 and the backwash pump 51. The purifying device 1 further includes a valve 55 connected between the primary side of the filter 10 and the waste tank 56. The washing water is fed to the secondary side of the filter 10 by the backwash pump 51 while the valve 52 is open and the valve 14 is closed. The washing water fed to the secondary side of the filter 10 flows to the primary side, backwashing the filter 10 and becoming waste liquid. The waste liquid produced by backwashing the filter 10 flows into the waste tank 56 while the valve 55 is open and the valve 13 is closed. In other words, in the backwash mode, the controller 32 of the purifying device 1 causes the valve 13 and the valve 14 to be closed, the valve 52 and the valve 55 to be open, and the backwash pump 51 to be driven.

In the backwash mode, the purifying device 1 may add a chemical to the washing water that is fed to the secondary side of the filter 10. The purifying device 1 further includes a valve 53 and a chemical solution 54. The chemical solution 54 is connected via the valve 53 to piping connecting the backwash pump 51 and the valve 52 through which the washing water flows. The purifying device 1 may add a chemical to the washing water in the backwash mode, while the valve 53 is open. In other words, in the backwash mode, the controller 32 of the purifying device 1 may cause the valve 53 to be open.

<Measurer 20>

The purifying device 1 samples a portion of the treated water in the filtration mode and measures microorganisms in the sample. Specifically, the purifying device 1 further includes a valve 21 that is connected to piping through which the treated water is fed. The measurer 20 samples a portion of the treated water via the valve 21. The measurer 20 may control sampling by controlling the opening and closing of the valve 21. The measurer 20 detects microorganisms in the collected sample and measures varieties of microorganisms detected, concentration or amount of microorganisms, and the like.

<<Sampling>>

The measurer 20 may, for example, sample a portion of the treated water according to the following procedure.

The measurer 20 may take a sample of a portion of the treated water when the quality of the treated water deteriorates. Specifically, the measurer 20 may monitor a water quality index value of the treated water and take a sample of a portion of the treated water when the water quality index value meets a condition. The measurer 20 may monitor water quality index values of the treated water, such as electrical conductivity (EC), flow cytometer particles, turbidity, chromaticity, chemical oxygen demand (COD), biochemical oxygen demand (BOD), total organic carbon (TOC), dissolved oxygen (DO), suspended solids (SS), chlorophyll concentration, total nitrogen (T-N), total phosphorus (T-P), organic pollutant concentration, adenosine triphosphate (ATP), and the like. In this way, the likelihood that the sample includes more microorganisms is higher. As a result, efficiency of detection of microorganisms in the sample may be improved.

When sampling a portion of the treated water, the measurer 20 may continuously sample the treated water while controlling the flow rate and flow speed of the treated water to be sampled. In this way, treated water may be sampled over a long period of time.

The measurer 20 may include equipment to cool a collected sample and store the sample at a controlled defined temperature. The measurer 20 may include cooling equipment for the piping from which the sample is taken. In this way, the accuracy of detection of microorganisms in the sample may be improved.

When collecting a portion of the treated water, the measurer 20 may control the flow rate of the piping from which the treated water is collected to be a defined rate or more, for example by adding water for dilution. In this way, the piping is less likely to become clogged.

The measurer 20 is not limited to the methods described above and may take samples by a variety of methods.

<<Detection of Microorganisms>>

The measurer 20 detects microorganisms in the sample. The measurer 20 may detect viruses, bacteria, protozoa, and the like as microorganisms. The measurer 20 may measure the size of microorganisms in the sample. The measurer 20 may, for example, acquire images of microorganisms in the sample and measure the size of the microorganisms.

The measurer 20 may measure the varieties of microorganisms in the sample. The measurer 20 may detect a variety of microorganism by, for example, amplifying a genetic nucleic acid of the microorganism in the sample by a polymerase chain reaction (PCR) method, performing annealing (hybridization) of the amplified nucleic acid with a fluorescent nucleic acid probe, and detecting light emission.

The measurer 20 may measure the amount or concentration of microorganisms in the sample. The measurer 20 may detect the amount or concentration of microorganisms based on a most probable number (MPN) method, for example.

The measurer 20 outputs the measurement result regarding microorganisms to the controller 32.

<Filter Evaluation>

The controller 32 evaluates the integrity of the filter 10 based on the measurement result obtained from the measurer 20 regarding microorganisms in a portion of the treated water taken as a sample. The integrity of the filter 10 includes filtration performance of the filter 10. The integrity of the filter 10 is reduced by a rupture or other damage to the membrane of the filter 10. The controller 32 may determine that damage has occurred to the membrane of the filter 10 when a defined variety of microorganism is detected in the sample. The controller 32 may determine that damage has occurred to the membrane of the filter 10 when a microorganism larger than a defined size is detected in the sample. The controller 32 may determine that damage has occurred to the membrane of the filter 10 when the amount of microorganisms in the sample is a defined amount or more. The controller 32 may determine that damage has occurred to the membrane of the filter 10 when the concentration of microorganisms in the sample is a defined concentration or more.

When the purifying device 1 includes one of the filter 10, the measurer 20 takes a sample from the secondary side of the one filter 10. The controller 32 is able to evaluate the integrity of the one filter 10 based on the measurement result of a sample by the measurer 20.

When the purifying device 1 includes a plurality of the filter 10 and the filters 10 are connected in parallel, the measurer 20 may take samples from piping on the secondary side of each of the filters 10. When samples corresponding to each of the filters 10 have been taken, the controller 32 is able to evaluate the integrity of each of the filters 10.

Figure 4:
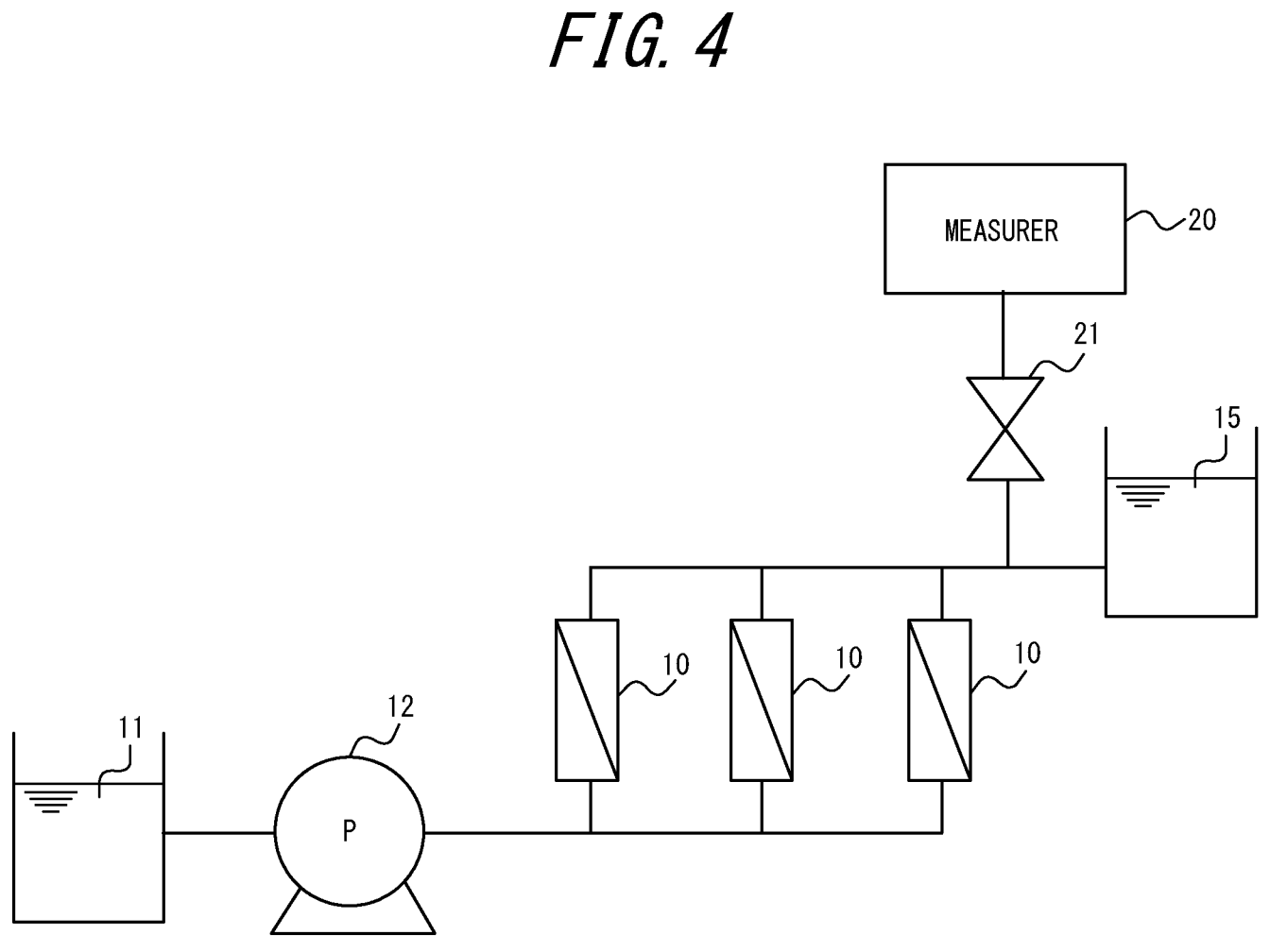

The measurer 20 may take a sample corresponding to a plurality of the filters 10 connected in parallel together from piping that joins at the secondary side of the plurality of filters 10. For example, as illustrated in FIG. 4, three of the filters 10 may be connected in parallel with each other. In other words, the purifying device 1 may include a plurality of the filters 10 connected in parallel with each other. The number of the filters 10 is not limited to three, and may be two, four, or more. In the filtration mode, the purifying device 1 feeds untreated water stored in the water storage tank 11 to the filters 10 that are connected in parallel by the filtration pump 12, and feeds the treated water filtered by the filters 10 to the water storage tank 15. The measurer 20 samples a portion of the treated water via the valve 21. In the example illustrated in FIG. 4, the valve 21 is configured to allow the measurer 20 to collectively sample treated water filtered by a plurality of the filters 10 from a pipe where the secondary side of each of the filters 10 connected in parallel join together. In other words, the measurer 20 is able to collectively sample treated water filtered by a plurality of the filters 10 via the valve 21. When collectively sampling from a plurality of the filters 10 connected in parallel, the controller 32 is able to evaluate the integrity of the plurality of the filters 10 connected in parallel as a whole. When the integrity as a whole of the plurality of the filters 10 connected in parallel is reduced, the controller 32 is able to determine that the integrity of at least one of the plurality of the filters 10 is reduced. In this way, by evaluating the integrity as a whole of the plurality of the filters 10 based on sampling from the plurality of the filters 10 connected in parallel, the time, cost, and the like spent on the evaluation of the filters 10 may be reduced. As a result, the convenience of the purifying device 1 that has the filters 10 is improved.

When the purifying device 1 includes a plurality of the filters 10 and the filters 10 are connected in series, the measurer 20 may take samples from the secondary side of each of the filters 10. The controller 32 is able to evaluate the integrity of each of the filters 10 based on the measurement result of samples taken from the secondary side of the filters 10. In a case where the filters 10 are connected in series, the filters 10 may include reverse osmosis membranes.

When the controller 32 determines that the integrity of the filter 10 is decreasing, the controller 32 may stop the operation in the filtration mode of the purifying device 1.

The controller 32 may output the evaluation result of the evaluation of the integrity of the filter 10. The controller 32 may output an alarm upon determining that the integrity of the filter 10 is decreasing. The controller 32 may output information as an alarm to inform a user when to replace the filter 10. The controller 32 may output information as an alarm to inform a user that operation in the filtration mode needs to be stopped. In this way, the need for maintenance, such as replacement of the filter 10, becomes clear. As a result, the convenience of the purifying device 1 is improved.

The controller 32 may determine that the integrity of the filter 10 is decreasing and output an alarm when an alarm condition is met. The alarm condition may include, for example, that a particle size of detected microorganisms is greater than a defined value in the measurement result of the measurer 20. The defined value may be based on the filtration performance of the filter 10. The defined value may be set to a value equal to or smaller than the pore diameter of the filter membrane of the filter 10, for example. The alarm condition may include, for example, that a specific variety of microorganism is detected in the measurement result of the measurer 20. The alarm condition may include that the concentration of a detected microorganism is equal to or more than a defined concentration. The alarm condition may include, but is not limited to, a variety of conditions.

<Example Procedures of Filter Evaluating Method>

Figure 5:
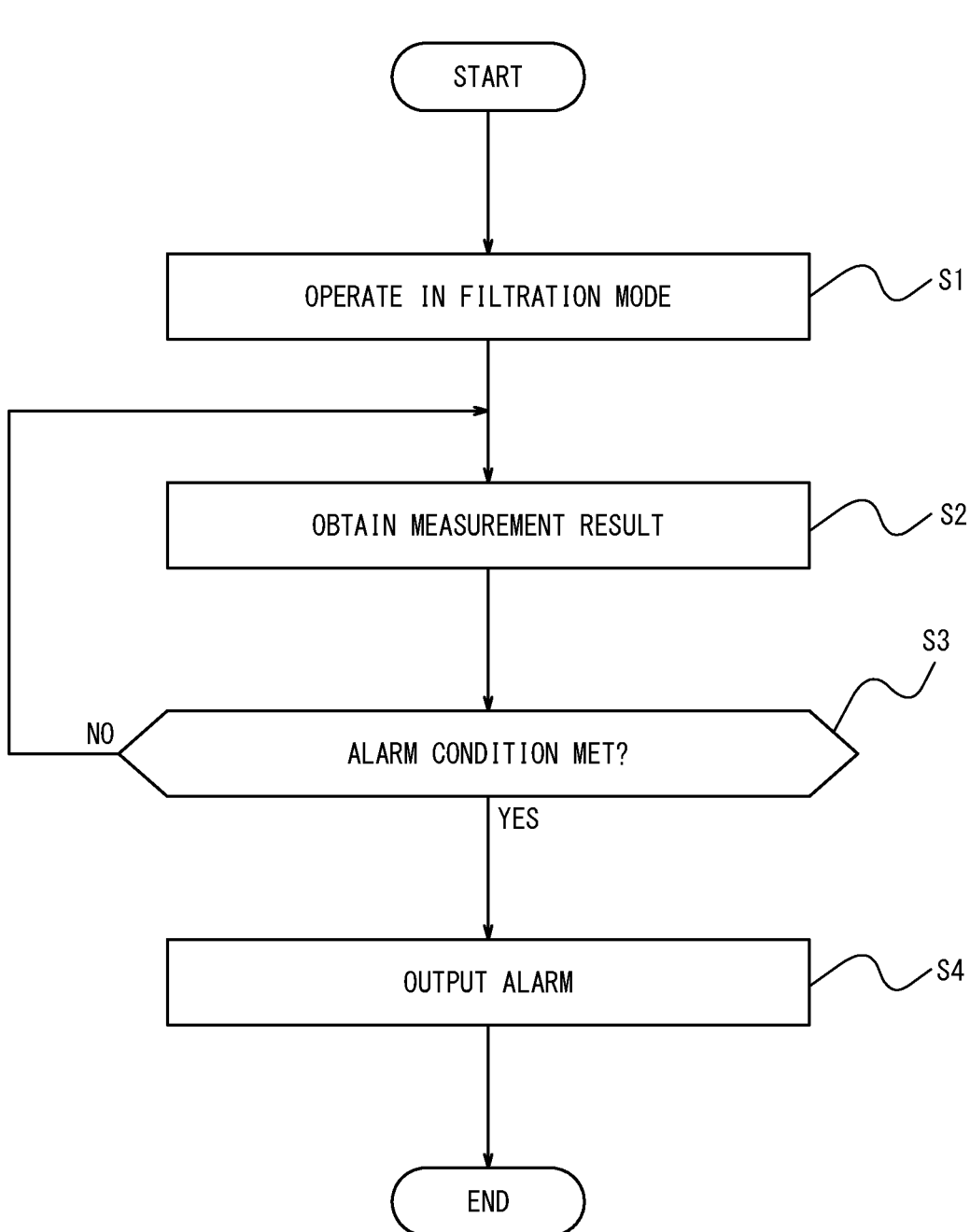
FIG. 5 is a flowchart illustrating example procedures of a filter evaluating method according to an embodiment.

The filter evaluating method according to an embodiment of the present disclosure may be performed according to the procedures of the flowchart illustrated in FIG. 5. The controller 32 of the purifying device 1 may perform the filter evaluating method. Further, the controller 32 may perform the filter evaluating method as the controller 32 of the filter evaluating device 30. The filter evaluating method may be realized as a filter evaluating program to be executed by a processor constituting the controller 32. The filter evaluating program may be stored on a non-transitory computer-readable storage medium.

The controller 32 causes the purifying device 1 to operate in the filtration mode (step S1). The controller 32 obtains a measurement result regarding microorganisms from the measurer 20 (step S2). The controller 32 determines whether the measurement result meets an alarm condition of the filter 10 (step S3). When the measurement result does not meet the alarm condition (step S3: NO), the controller 32 may return to the procedure of step S2 to obtain a measurement result. When the measurement result meets the alarm condition (step 3: YES), the controller 32 may output an alarm (step S4). After execution of the procedure in step S4, the controller 32 ends execution of the procedures of the flowchart in FIG. 5.

<Review>

As described above, according to the filter evaluating device 30 and the filter evaluating method pertaining to the present embodiment, the integrity of the filter 10 is evaluated based on the measurement result of measuring microorganisms in the treated water. The measurement of microorganisms is performed while the purifying device 1 is operating in the filtration mode. In this way, the availability of the purifying device 1 may be improved. As a result, the convenience of the purifying device 1 is improved.

In terms of managing water quality and removal performance related to microorganisms in the water of a filtration system using MF and UF membranes, the filtration quality of the filtration system is ascertained by evaluating the integrity of the filter 10. Further, the pathogenic risk of filtered water is ascertained. Further, filtered water quality of a filtration system using MF and UF membranes may be ascertained without performing PDT. Thus, the filtration system does not need to stop filtration for PDT. In this way, availability is improved, operation sequencing is simplified by not performing PDT, and the equipment required for PDT may be omitted. The purifying device 1 according to the present embodiment may be configured to perform PDT. By implementing PDT in addition to the filter evaluating method according to the present embodiment, the integrity of the filter 10 may be further assured. As a result, more robust water quality control may be achieved.

Other Embodiments

According to the present embodiment, the controller 32 of the purifying device 1 or the controller 32 of the filter evaluating device 30 obtains the measurement result of measuring microorganisms in the sample from the measurer 20. The measurement of microorganisms in the sample does not have to be performed by the measurer 20. For example, the measurement of microorganisms in the sample may be performed using a technique based on microorganism culturing or a molecular biology technique.

Evaluation of the integrity of the filter 10 by the controller 32 may be performed, for example, once a day or more frequently. In other words, measurement of microorganisms in samples may be performed once a day or more frequently. In the purifying device 1 according to the present embodiment, the evaluation of the integrity of the filter 10 may be performed while operating in the filtration mode. Therefore, even when evaluations are performed once a day or more frequently, the availability of the purifying device 1 is unlikely to decrease.

The present disclosure is not limited to the configurations specified in the embodiments described above, and various modifications are possible without departing from the scope of the claims. For example, the functions and the like included in each step may be reconfigured as long as no logical inconsistency arises. Multiple steps may be combined into one, and a single step may be split into more than one.

The invention claimed is:

1. A purifying device comprising a filter, a measurer and a controller, wherein the measurer is configured to:

amplify, by polymerase chain reaction (PCR) method, a genetic nucleic acid of viruses in water filtered by the filter; and detect varieties of the viruses in the water filtered by the filter, by performing hybridization of an amplified nucleic acid with a fluorescent nucleic acid and detecting light emission, and the controller is configured to evaluate the integrity of the filter based on a measurement result regarding the viruses in the water filtered by the filter, and output information regarding an evaluation result.

2. The purifying device according to claim 1, wherein the controller is configured to output an alarm regarding the filter when the water filtered by the filter includes viruses having a particle size of a defined value or more, the defined value determined based on filtration performance of the filter.

3. The purifying device according to claim 2, wherein controller is configured to output the alarm regarding the filter when a specific variety of microorganism is detected as a microorganism in the water filtered by the filter.

4. The purifying device according to claim 1, wherein the controller is configured to output an alarm regarding the filter when a specific variety of microorganism is detected as a microorganism in the water filtered by the filter.

5. The purifying device according to claim 1, comprising the filter in a plurality, each connected in parallel with each other, and further comprising:

a valve configured to allow the measurer to collectively sample water filtered by the plurality of filters from a pipe that merges flow on a secondary side of the plurality of filters.

6. The purifying device according to claim 1, wherein the measurer is configured to detect amount or concentration of the viruses in the water filtered by the filter based on a most probable number (MPN) method.

7. The purifying device according to claim 1, wherein viruses, which are detected by the measurer, cannot be removed by the filter.

8. The purifying device according to claim 7, wherein viruses, which are detected by the measurer, are smaller than *Cryptosporidium*.

9. A-purifying method comprising:

amplifying, by polymerase chain reaction (PCR) method, a genetic nucleic acid of viruses in water filtered by a filter;

detecting varieties of the viruses in the water filtered by the filter, by performing hybridization of an amplified nucleic acid with a fluorescent nucleic acid and detecting light emission; and evaluating the integrity of a filter based on a measurement result of measuring viruses in water filtered by the filter; and outputting information regarding an evaluation result.

* * * * *